United States Patent
Yanai et al.

(10) Patent No.: US 9,192,705 B2
(45) Date of Patent: Nov. 24, 2015

(54) PERCUTANEOUS CABLE WITH REDUNDANT CONDUCTORS FOR IMPLANTABLE BLOOD PUMP

(71) Applicant: THORATEC CORPORATION, Pleasanton, CA (US)

(72) Inventors: Masamichi Yanai, Ann Arbor, MI (US); Himanshu K. Bhatt, Ann Arbor, MI (US)

(73) Assignee: Thoratec Corporation, Pleasanton, CA (US)

( * ) Notice: Subject to any disclaimer, the term of this patent is extended or adjusted under 35 U.S.C. 154(b) by 107 days.

(21) Appl. No.: 13/849,704

(22) Filed: Mar. 25, 2013

(65) Prior Publication Data

US 2014/0288352 A1 Sep. 25, 2014

(51) Int. Cl.
*A61M 1/12* (2006.01)
*A61M 1/10* (2006.01)

(52) U.S. Cl.
CPC ............ *A61M 1/122* (2014.02); *A61M 1/101* (2013.01); *A61M 1/127* (2013.01)

(58) Field of Classification Search
CPC . A61M 1/101; A61M 1/1037; A61M 1/1086; A61M 1/122; A61M 1/127
USPC ..................... 600/16; 623/3.1, 3.15
See application file for complete search history.

(56) References Cited

U.S. PATENT DOCUMENTS

| | | | |
|---|---|---|---|
| 4,434,389 A * | 2/1984 | Langley et al. .......... 318/400.41 | |
| 4,665,896 A * | 5/1987 | LaForge .............. A61M 1/1086 600/17 | |
| 4,895,557 A | 1/1990 | Moise et al. | |
| 5,613,935 A * | 3/1997 | Jarvik .................... A61M 1/101 600/16 | |
| 6,351,048 B1 * | 2/2002 | Schob .................... A61M 1/101 310/68 B | |
| 6,486,405 B2 | 11/2002 | Lin | |
| 6,785,576 B2 | 8/2004 | Verness | |
| 6,925,334 B1 | 8/2005 | Salys | |
| 7,734,354 B1 | 6/2010 | Cox | |
| 8,382,830 B2 | 2/2013 | Maher et al. | |
| 8,388,384 B2 | 3/2013 | Cotter | |
| 8,652,024 B1 | 2/2014 | Yanai et al. | |
| 2001/0002234 A1 * | 5/2001 | Woodard ............... A61M 1/101 415/182.1 | |
| 2005/0025630 A1 * | 2/2005 | Ayre ...................... A61M 1/101 417/53 | |
| 2010/0305692 A1 * | 12/2010 | Thomas .................. A61M 1/10 623/3.1 | |
| 2011/0071336 A1 | 3/2011 | Yomtov et al. | |

(Continued)

OTHER PUBLICATIONS

International Search report and Written Opinion from PCT/US2014/012448 mailed on Feb. 19, 2014, 8 pages.

(Continued)

*Primary Examiner* — Christopher D Koharski
*Assistant Examiner* — Jeremiah Kimball
(74) *Attorney, Agent, or Firm* — Kilpatrick Townsend & Stockton LLP

(57) ABSTRACT

A blood pump system for left ventricle assist has an implantable pump unit having a multiphase stator having a plurality of windings connected between respective junctions for forming first, second, and third phases. An external control unit comprises an H-bridge inverter having first, second, and third phase legs. A percutaneous cable is provided having first, second, and third parallel pairs of redundant conductors. Each conductor pair is connected between a respective phase leg and a respective junction. The conductors are arranged concentrically around a cable core so that individual conductors of each pair are separated by at least one conductor of a different conductor pair.

5 Claims, 3 Drawing Sheets

(56) References Cited

U.S. PATENT DOCUMENTS

2011/0160516 A1 6/2011 Dague et al.
2013/0289334 A1* 10/2013 Badstibner et al. ............ 600/16
2014/0200389 A1* 7/2014 Yanai et al. .................... 600/16

OTHER PUBLICATIONS

International Search Report and Written Opinion from PCT/US2014/031415 mailed on Aug. 8, 2014, 13 pages.

* cited by examiner

PERCUTANEOUS CABLE WITH REDUNDANT CONDUCTORS FOR IMPLANTABLE BLOOD PUMP

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to circulatory assist devices, and, more specifically, to enhanced reliability of a cable connection between an external control unit and an implanted pump unit.

Many types of circulatory assist devices are available for either short term or long term support for patients having cardiovascular disease. For example, a heart pump system known as a left ventricular assist device (LVAD) can provide long term patient support with an implantable pump associated with an externally-worn pump control unit and batteries. The LVAD improves circulation throughout the body by assisting the left side of the heart in pumping blood. One such system is the DuraHeart® LVAS system made by Terumo Heart, Inc., of Ann Arbor, Mich. The DuraHeart® system employs a centrifugal pump with a magnetically levitated impeller to pump blood from the left ventricle to the aorta. An electric motor magnetically coupled to the impeller is driven at a speed appropriate to obtain the desired blood flow through the pump.

A typical cardiac assist system includes a pumping unit, electrical motor (e.g., a brushless DC motor integrated into the pump), drive electronics, microprocessor control unit, and an energy source such as rechargeable batteries and/or an AC power conditioning circuit. The system may be implantable, either fully or partially. The goal of the control unit is to autonomously control the pump performance to satisfy the physiologic needs of the patient while maintaining safe and reliable system operation. A control system for varying pump speed to achieve a target blood flow based on physiologic conditions is shown in U.S. Pat. No. 7,160,243, issued Jan. 9, 2007, which is incorporated herein by reference in its entirety.

A typical pump motor employed for a blood pump is a three-phase permanent magnet electric motor that can be driven as a brushless DC or a synchronous AC motor without any position sensor. The need for a position sensor is avoided by controlling motor operation with one of a variety of methods that use the measured stator phase currents to infer the position. Vector control is one typical method used in variable frequency drives to control the torque and speed of a three-phase electric motor by controlling the current fed to the motor phases. This control can be implemented using a fixed or variable voltage drive delivered via an inverter comprised of pulse width modulated H-bridge power switches arranged in phase legs. Reliability, fault detection, and fault tolerance are important characteristics of an electrically-powered blood pump, drive system, and cable, and it would be desirable to improve each of them.

Application Ser. No. 13/418,447, filed Mar. 13, 2012, entitled "Fault Monitor For Fault Tolerant Implantable Pump," now U.S. Pat. No. 8,837,096, which is hereby incorporated by reference, discloses a fault-tolerant inverter/cable system wherein redundant inverter legs are coupled to the motor phases by redundant, parallel conductors between the external unit and the implanted pump. For a three-phase motor, the redundant interconnect system includes six conductors in the cable. By monitoring the equality of the current and/or voltage of the two conductors on the same phase, a fault or impending fault can be detected for each individual conductor.

The redundant conductors of a cable pair would typically have their ends attached to the same terminals (e.g., at respective terminal connectors at the implanted pump and the external control unit). Since the end connections are made in common or are closely spaced, the redundant conductors of each pair have been taken adjacent to each other within the cable.

SUMMARY OF THE INVENTION

It has been discovered that the conventional approach of placing the redundant conductors adjacent to one another can lead to premature failure of the redundancy. In a typical failure mode, flexing of the cable may lead to a cracking or tearing along a particular edge of the cable which penetrates one of the conductors. As that conductor fails, all the current flow for the corresponding phase flows through the redundant conductor. Integrity of the remaining conductor becomes critical, but it has been found that the placement adjacent to the failed conductor may shorten the expected time-to-failure of the remaining good conductor.

In one aspect of the invention, a blood pump system for left ventricle assist comprises an implantable pump unit having a multiphase stator having a plurality of windings connected between respective junctions for forming first, second, and third phases. An external control unit comprises an H-bridge inverter having first, second, and third phase legs. A percutaneous cable is provided having first, second, and third parallel pairs of redundant conductors. Each conductor pair is connected between a respective phase leg and a respective junction. The conductors are arranged concentrically around a cable core so that individual conductors of each pair are separated by at least one conductor of a different conductor pair.

DETAILED DESCRIPTION OF PREFERRED EMBODIMENTS

Figure 1:
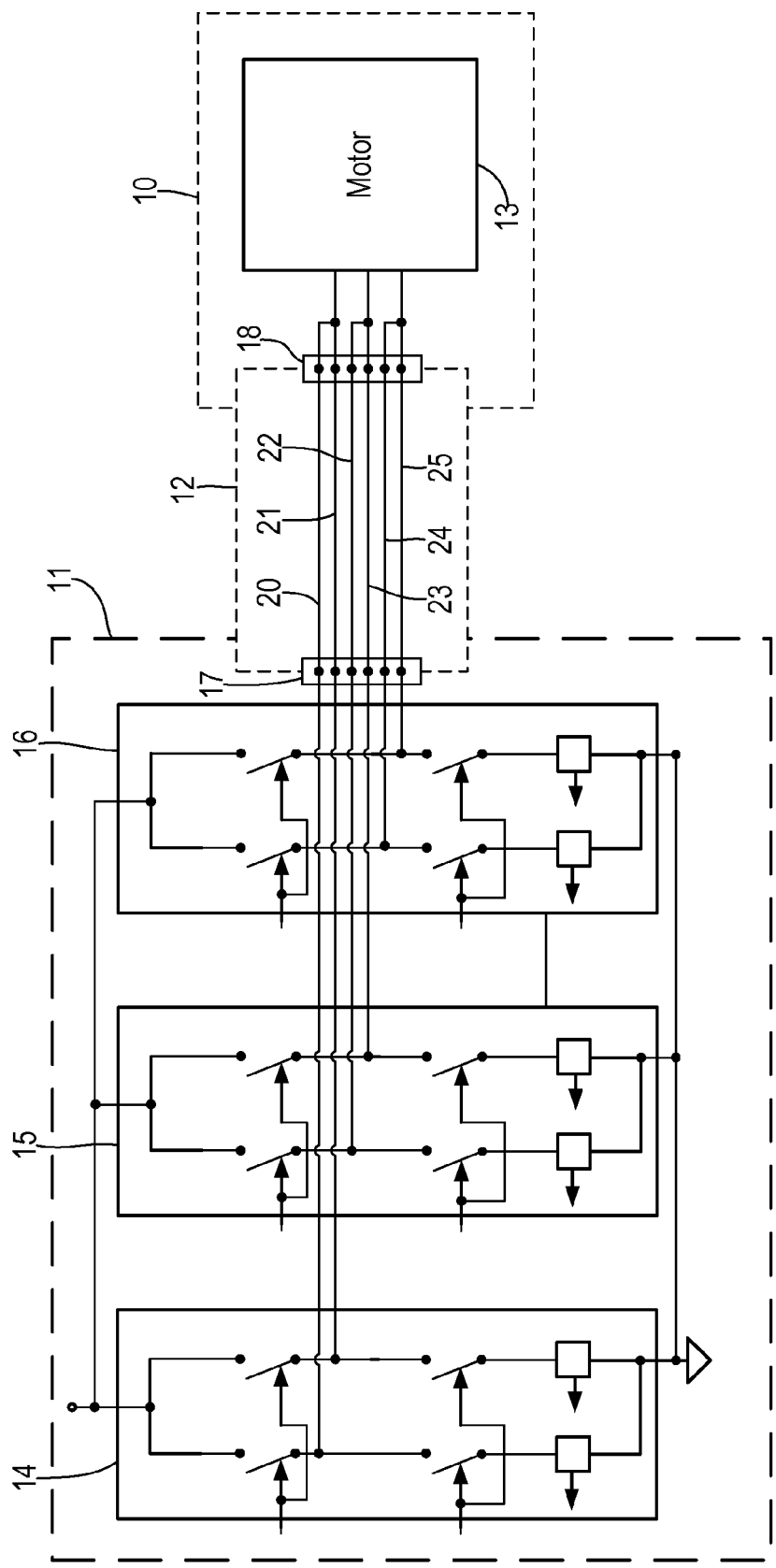
FIG. 1 is a schematic diagram showing redundant phase legs and cable conductors employed in one embodiment of the present invention.

FIG. 1 shows a ventricular assist system in which a pump unit 10 is driven by an inverter 11 in an external control unit. A percutaneous cable 12 couples inverter 11 to a motor 13 in pump unit 10. Inverter 11 has a first phase 14, a second phase 15, and a third phase 16. Each phase has a pair of redundant phase legs with respective upper and lower power switches. Each phase leg is connected to a respective terminal on a terminal block 17. Cable 12 includes conductors 20-25 connected between terminal block 17 and a terminal block 18 in pump unit 10. Conductors 20 and 21 redundantly carry the drive signals for phase 14, conductors 22 and 23 redundantly carry the drive signals for phase 15, and conductors 24 and 25 redundantly carry the drive signals for phase 16. The redundant drive signals are joined in pump unit 10 and are coupled to motor 13 in order to drive respective motor windings.

Figure 2:
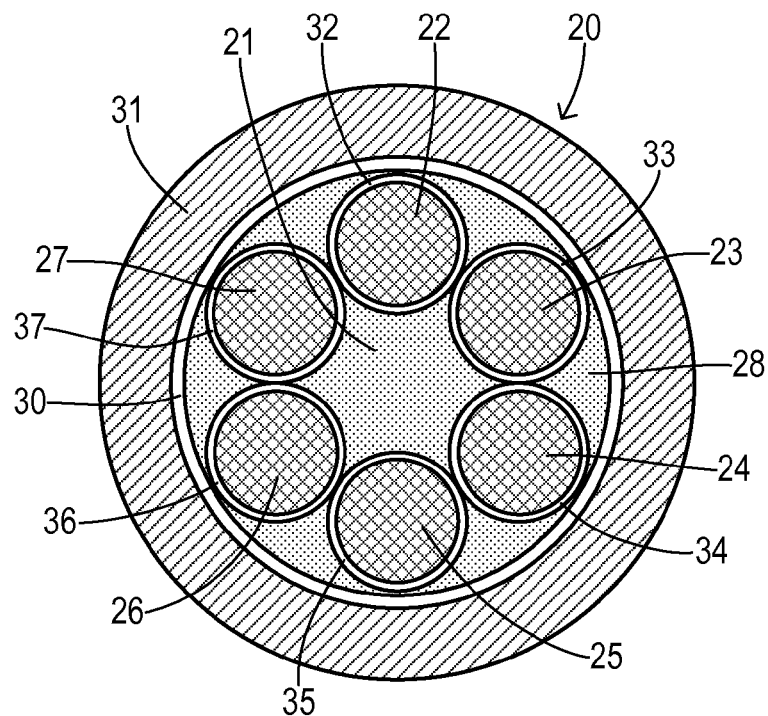
FIG. 2 is a radial cross section of a multi-phase percutaneous cable used in the present invention.
Figure 3:
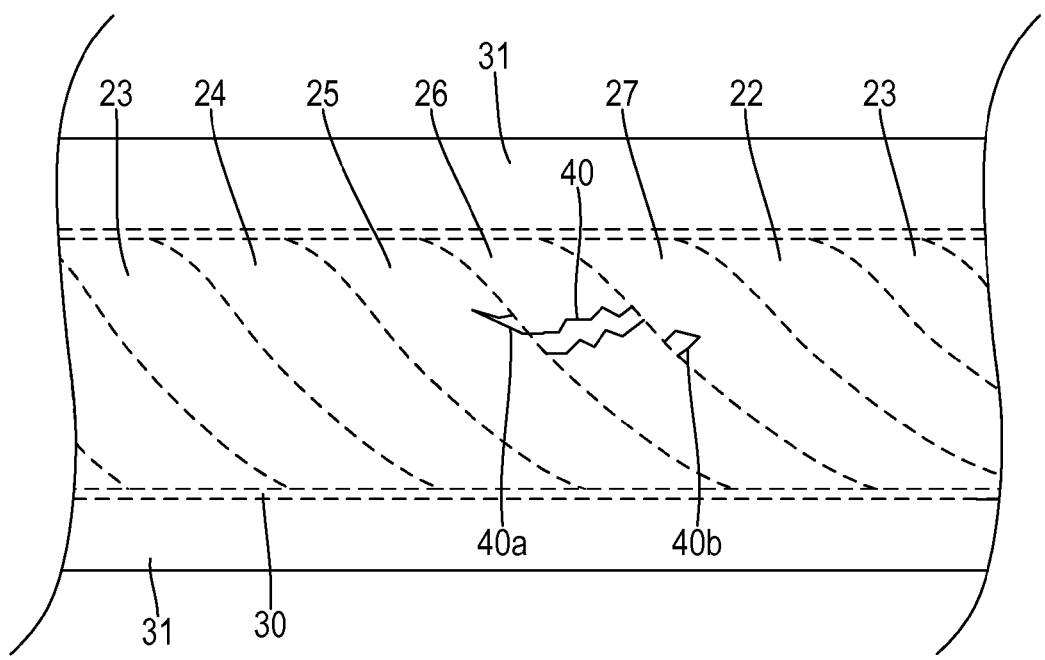
FIG. 3 is a longitudinal side view of the cable of FIG. 2.

Referring to FIG. 2, a percutaneous cable 20 is shown in radial cross-section having six separate conductors 22-27 arranged concentrically around a cable core 21. Cable core 21 may be comprised of a conventional moldable material such as a fiber fill having an appropriate strength and flexibility. Core 21 may be extruded between and around conductors 22-27 as shown at 28. Each individual conductor 22-27 is preferably comprised of a large number of twisted wire strands enclosed in a separate insulating cover 32-37. A liner 30 and an outer jacket 31 may also be provided around the conductors and cable core to provide a highly reliable and durable cable structure.

Cable 20 is of a generally cylindrical shape. It is capable of being sterilized for implantation and is made of biocompatible materials with sufficient flexibility and strength to perform as a percutaneous cable. Conductors 22-27 may be preferably helically twisted within cable 20 to enhance the flexibility. After repeated flexing during in-service usage, however, a fracture or crack 40 may eventually appear in one of the individual conductors such as conductor 26. As a result of fracture 40, mechanical stress becomes concentrated in that location since the overall cable structure is weakened. Due to the concentrated stress and the loss of localized strength, increased forces are applied to the adjacent conductors so that the fracture may spread at 40a in conductor 25 and 40b in conductor 27. Thus, the likelihood increases that the next conductor to fail will be one of the adjacent conductors.

Once one conductor of a redundant pair has failed, the remaining conductor of that pair becomes more critical for continued system operation than conductors of another pair for which neither conductor has yet faulted. Thus, the present invention adopts a connection scheme for the redundant conductors in which individual conductors of each pair are separated by at least one conductor of a different conductor pair in the concentric arrangement around the cable core.

Figure 4:
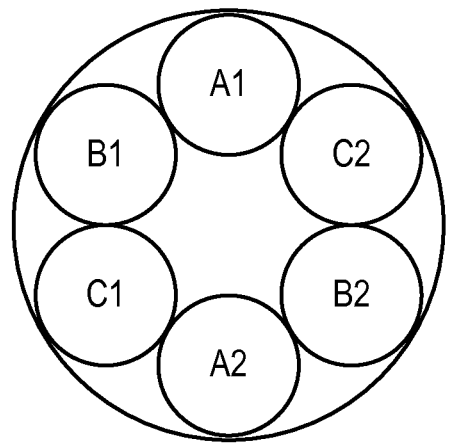
FIG. 4 is a radial cross section showing a first embodiment for pairing redundant conductors.

In the system of the present invention, the external control unit includes an H-bridge inverter having first, second, and third phase legs designated A, B, and C. Each phase leg must be connected to a respective junction between first, second, and third phases of a multiphase stator in an implantable pump. Each conductor pair of the cable connects a respective phase leg to a respective junction. In a preferred embodiment as shown in FIG. 4, conductors A1 and A2 of a redundant conductor pair are placed in diametric opposition. Likewise, conductors B1 and B2 for phase B and conductors C1 and C2 for phase C are each placed in diametric opposition. Thus, each conductor of any particular pair is separated from its mate by at least two conductors from other redundant pairs. It should be noted that the percutaneous cable may include more than six conductors. For example, there may be more than three phase pairs of conductors (i.e., the pump motor may have more than three phases) or the cable may also include conductors carrying other types of signals (e.g., sensor signals). Preferably, such additional conductors may also be arranged concentrically around the cable core.

With the arrangement in FIG. 4, when a fracture occurs at any particular location along the cable, an effected conductor beneath or involving the fracture will have its redundant conductor partner on the diametrically opposite side of the cable so that the partner will be least affected by any concentrated or increased stress that is created by continued flexing of the cable.

Figure 5:
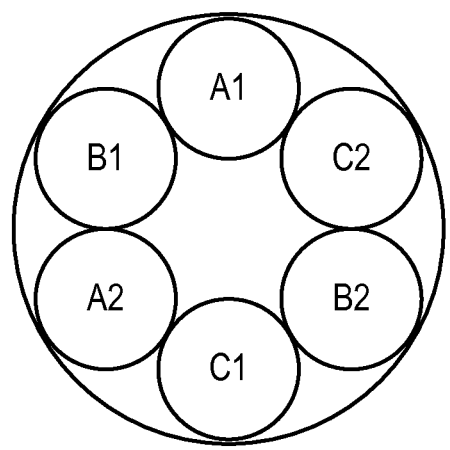
FIG. 5 is a radial cross section showing a second embodiment for pairing redundant conductors.

FIG. 5 shows an alternative embodiment of the arranged conductor pairs in which some or all of the conductor pairs are not in full diametric opposition yet they are still separated by at least one conductor of a different conductor pair. Thus, a conductor pair A1/A2 is separated by an intervening conductor B1 for the phase B pair. Likewise, a pair of conductors C1/C2 is separated by a conductor B2. As a result of moving apart the conductors of each redundant pair, the onset of a total failure by the fracturing of both conductors in a single pair is delayed since the failure of one conductor does not immediately increase the stress experienced by the other conductor of the same pair.

What is claimed is:

1. A blood pump system for left ventricle assist comprising:
   an implantable pump unit having a multiphase stator having a plurality of windings connected between respective junctions for driving first, second, and third electrically parallel pairs of redundant conductors in corresponding first, second, and third phases;
   an external control unit comprising an H-bridge inverter having first, second, and third phase legs; and
   a percutaneous cable having the first, second, and third electrically parallel pairs of redundant conductors, wherein each conductor pair is connected between a respective phase leg within the external control unit and a respective common junction within the implantable pump unit, wherein the conductors are arranged concentrically around a cable core so that individual conductors of each pair are separated by at least one conductor of a different conductor pair.

2. The system of claim 1 wherein the concentric arrangement of the conductors places the individual conductors of each pair in diametric opposition.

3. The system of claim 1 wherein the cable is cylindrically-shaped, and wherein the individual conductors are helically twisted within the cable.

4. The system of claim 1 wherein the cable further comprises an outer jacket surrounding the concentrically-arranged conductors.

5. A blood pump system for left ventricle assist, comprising:
   an implantable pump unit having a multiphase stator having a plurality of windings connected between respective junctions for driving first, second, and third electrically parallel pairs of redundant conductors in corresponding first, second, and third phases;
   an external control unit comprising an H-bridge inverter having first, second, and third phase legs; and
   a percutaneous cable having the first, second, and third electrically parallel pairs of redundant conductors, wherein each conductor pair is connected between a respective phase leg within the external control unit and a respective common junction within the implantable pump unit, wherein the conductors are arranged concentrically around a cable core so that individual conductors of each pair are separated by at least one conductor of a different conductor pair and are placed in diametric opposition.

* * * * *